United States Patent [19]
Podolsky

[11] Patent Number: 5,725,483
[45] Date of Patent: Mar. 10, 1998

[54] MASSAGING DEVICE

[76] Inventor: Grigory Podolsky, 33-34 77th. St. #5-H, Jackson Heights, N.Y. 11372

[21] Appl. No.: 199,669

[22] Filed: Feb. 22, 1994

[51] Int. Cl.[6] .......................... A61H 1/00; A61H 15/02; A46B 11/02

[52] U.S. Cl. .................. 601/15; 601/87; 601/113; 601/114; 601/17; 601/159; 601/135

[58] Field of Search ............ 601/87, 112–114, 601/17, 154, 159, 160, 134, 135, 94, 95, 15; 600/9

[56] References Cited

U.S. PATENT DOCUMENTS

| | | | |
|---|---|---|---|
| 1,577,751 | 3/1926 | Paschall | 601/112 |
| 1,931,849 | 10/1933 | Matson | 601/112 X |
| 2,043,114 | 6/1936 | Ruttger-Pelli | 601/173 |
| 3,733,634 | 5/1973 | Golbe | 601/114 X |
| 3,968,789 | 7/1976 | Simoncini | 601/112 X |
| 3,993,052 | 11/1976 | Miyahara | 128/46 |
| 3,994,290 | 11/1976 | Springer et al. | 601/154 X |
| 4,027,348 | 6/1977 | Flowers et al. | 601/114 X |
| 4,520,163 | 5/1985 | Fedders | 601/112 |
| 4,571,768 | 2/1986 | Kawashima | 600/9 |
| 4,744,350 | 5/1988 | Sato | 601/1 X |
| 4,777,940 | 10/1988 | Yamasaket et al. | 128/46 |
| 4,785,798 | 11/1988 | Yamasaket et al. | 128/46 |
| 4,918,818 | 4/1990 | Hsieh | 30/34.05 |
| 5,092,041 | 3/1992 | Podolosky | 30/41 |
| 5,103,089 | 4/1992 | Deluca et al. | 601/135 |
| 5,103,560 | 4/1992 | Podolosky | 30/41 |
| 5,105,802 | 4/1992 | Pokorny | 601/131 |
| 5,133,130 | 7/1992 | Podolosky | 30/41 |

*Primary Examiner*—Danton D. DeMille

[57] ABSTRACT

A massaging device includes a plurality of displaceable massaging members mounted on a universal head, each of the massaging elements is rotatable about a respective orbit and movable toward and away from a center of the head head, and magnetic elements creating magnetic vortexes upon displacement of the massaging members.

12 Claims, 1 Drawing Sheet

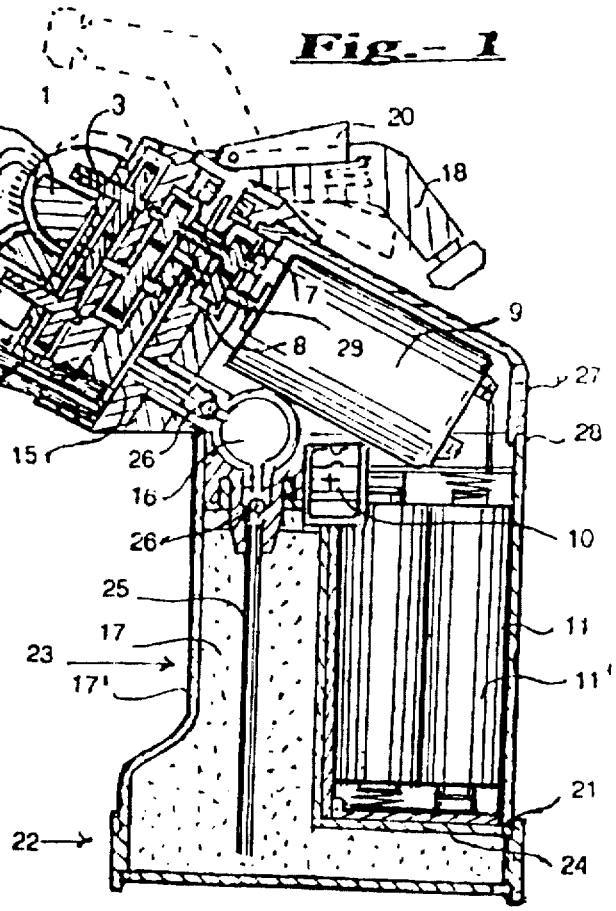
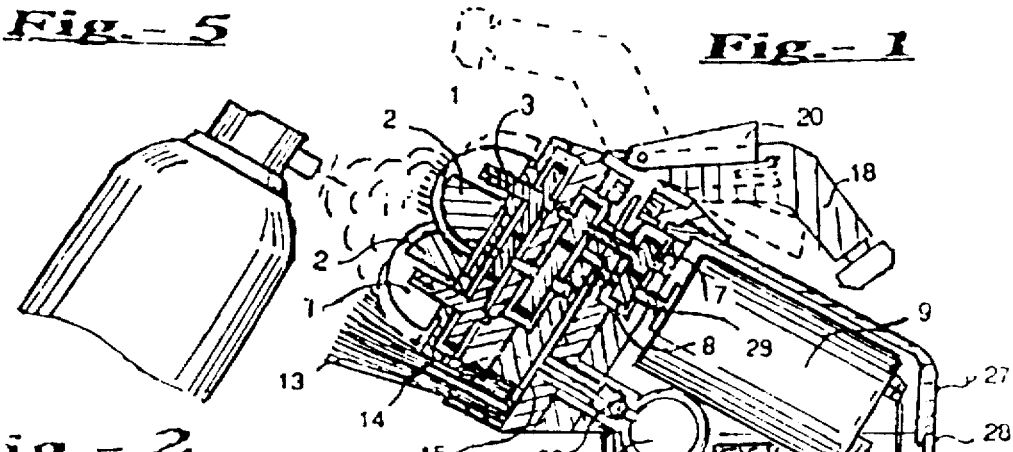
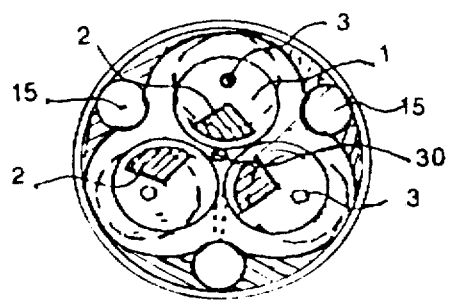
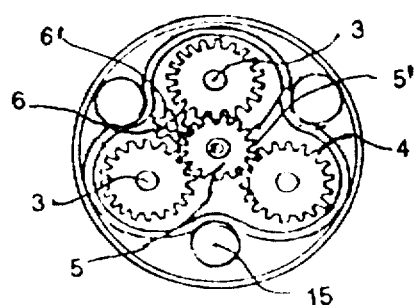
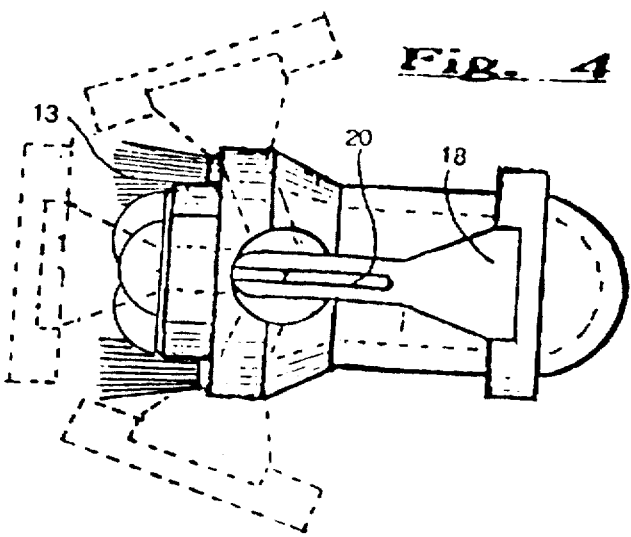
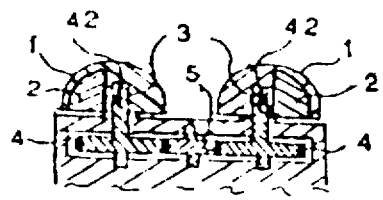

MASSAGING DEVICE

FIELD OF THE INVENTION

The present invention generally relates to a massaging device, and more particularly, to a shaving device provided with a massaging means for treating skin before and after shaving.

BACKGROUND OF THE INVENTION

Shaving devices of different types are known in the art. The devices most relevant to the presently invented shaving device are described in U.S. Pat. Nos. 5,133,130, 5,103,560 and 5,092,041. Yet regardless of a type of the shaving device the very action of shaving affects the human skin detrimentally and causes irritation thereof and even leads to an incurable damage. Preventive measures are also well known and usually include massaging the skin before shaving and smoothing the former with an aftershaving lotion. While these measures can be effective, the preshaving massage usually does not condition the skin adequately enough for further shaving because of the variety of reasons. Not the least of them is the use of a separate massaging means.

OBJECT OF THE INVENTION

It is therefore the principal object of the present invention to provide an effective massaging device capable of effectively soothing the skin.

Another object of the present invention is to provide a shaving device capable of massaging the skin while delivering the shaving cream thereunto.

Yet another object of the present invention is to provide the shaving device formed with a means for positioning the razor blade holder according to a user's convenience.

SUMMARY OF THE INVENTION

A basic structure of the device according to the invention is described in the above mentioned patents and includes a hollow handle with an inner chamber, a head, means for supplying the shaving cream on the user's skin, shaving means for shaving the user's hair and massaging means for treating the skin and distributing the shaving cream or an aftershaving lotion upon applying thereof.

The critical structure of the newly invented device is the provision of a plurality of semi-spherical members which are rotatable on offset centers with the ball bearings. In other words during the rotation the semi-spherical members move toward and away from a center along respective orbits creating thereby effective mixing of the shaving cream during shaving.

According to one of the embodiments the rotatable members are removable semi-spherical balls which are equally effective in massaging the skin before or/and after shaving as well as in delivering and distributing the shaving cream. The balls can be made of any magnetizable material improving the massaging effect by creating magnetic vortexes. On the other hand, the balls can be provided with magnet inserts mounted on the head.

Another embodiment according to the invention is directed to the use of brushes mounted rotatably about the offset axes on the head. The device is provided with a receiving means mounted on respective shafts for receiving either the semi-sphere balls or the brushes provided with respective connectors interacting with the receiving means. In both embodiment it is possible to provide a means for alternating clockwise direction of the movement of the spheres and counterclockwise one.

Additionally to the above described features, the device according to the invention is also provided with a displaceable razor blade formed, in turn, with a lever mounted pivotally thereon. The lever is mounted on the razor support so that the user can easily utilize only one hand for all necessary operations during massaging and shaving. While the description relates primarily to the shaving device the basic structure can utilized by massaging means.

BRIEF DESCRIPTION OF THE DRAWING

The above and other objects, features and advantages will become more readily apparent from the following description, references being made to the accompanying drawing in which:

FIG. 1 is an elevational sectional side view of the device according to the invention;

FIG. 2 is a front view of the universal head;

FIG. 3 is cross-sectional view of the universal head;

FIG. 4 is a top view of the device with the rotatable lever;

FIG. 5 is a shaving cream container cooperating with the device according to the invention; and FIG. 6 is a sectional side view of the universal head.

SPECIFIC DESCRIPTION

The device as seen in FIG. 1 includes a handle 17 removably supported on a support 21 having generally a flat bottom. The interior of the handle is hollow and is formed with a wider base part 22 and a narrow part 23 having generally an oval cross section. A bottom 24 is provided with any suitable connecting means as, for example, an outer thread cooperating with an inner thread for removing the bottom.

The interior is divided in two compartments extending at a distance from the bottom 24 and divided in two compartments 11 and 17'. The compartment 11 is designed for receiving actuating means such as, for example, a battery or accumulator. The compartment 17' is basically a reservoir for storing a flowable substance such as a lotion or a cologne which is used for massaging and shaving. The structure for supplying the substance to the brushes is well known and includes generally a pump 16 which is connected with the compartment 17' through a pipe means 25 immersed in the substance, and the valve means 26 for dosing the supply of the substance. The channel 15 formed upstream from the elastic pump and in flow communication with an outlet thereof is provided with a plurality of branches 15', 15" leading to respective brushes 13 for delivering the substance thereto. Each brush 13 has a respective central channel 14 communicating with the respective branch 15' and opening outwardly into respective brush for delivering the substance on the skin of a user. The provision of the multibranch channel defines uniform distribution of the substance among a plurality of brushes. The brushes, in turn, are formed with respective central channels communicating with branches.

A housing of the device further includes a top portion 27 mounted on the handle 17 and inclined to a vertical. The connection between the handle and the top portion can be rigid as shown in FIG. 1 with respective portion overlapping one another. Yet it is possible to use any suitable means, for example, pins 28 for mounting the top portion pivotally. The top portion 27 also has a hollow interior traversed by the supply channel and receiving an actuating means, i.e. a motor 9 mounted on an inner wall of the top portion and formed with a driving shaft 29. As is said before either a battery or accumulator 11' can be used to actuate the motor. The accumulator is easily rechargeable by plugging it in a wall AC socket. A switch 10 is used for connecting the motor with the battery or accumulator. Advantageously, the switch 10 is a double throw switch so it can provide a change of polarity leading, in turn, to changing a direction of rotation of the driving shaft 29 with subsequent changing in direction of rotation of the semi-spherical members 1.

A head 27 clearly illustrated in FIGS. 2 and 3 is formed preferably as a one-piece integral member made of a heat retaining material and provided with recesses receiving the brushes 13 The massaging semi-spherical members 1 are mounted rotatably about offset axes 3 with ball bearings. During the rotation the members produce the action of a mixer by approaching the center 30 (FIG. 2) with the orbits bordering with one another and then moving away therefrom. As shown in FIG. 5, a shaving cream container applies the cream in the vicinity of the members which subsequently mix it without using the brushes. The use of members can be utilized before applying the cream or after shaving by either applying a lotion or cologne from a separate container or even providing a means for delivering the substance from the reservoir 17' directly to a periphery of the members.

Generally the members i are made of a magnetizable material. However, if the members do not have magnetic property removable magnetic inserts 2 are mounted on the head which is provided with formations receiving the inserts or directly on the members. Regardless of any particular embodiment described above, the sole function of magnetic properties is to create magnetic vortexes upon displacement of the members 1.

As is shown in FIG. 3 a pinion 6 is mounted rotatably fixedly on a shaft 6' provided with a respective pinion 7 having a diameter larger than the one of the pinion 6 and meshing, in turn, with a pinion 8 which has a lesser diameter than the pinion 7. The pinion 8 is mounted on the driving shaft 29 of the motor 9. The pinion 6 meshes with an intermediate pinion 5' with ball bearings 5 mounted on the intermediate pinion axis. The latter, in turn, engages pinions or planetary gears 4 mounted fixedly on shafts 3 offset from and parallel to respective axes of symmetry of the members 1. The system of pinions or gears forms a reducer decreasing a number of revolutions of the motor 9, so that the rotary speed of the members increases as a result of the reduced load applied to the motor.

FIG. 6 illustrates the semi-sphere elements 1 which are mounted on respective shafts 3. Each shaft is provided with a respective protrusion 40 engaging a formation in the member 3. An upper end of each shaft 3 is also formed with a slit 42 adding certain resilience to the shaft, so that the members 1 are easily removable and therefore can be replaced. The protrusions 40 urge against a respective inner surfaces formed in the member. The analogously functioning connecting means 13" can be provided on additional brushes 13' which are simply mounted on the shafts for performing corresponding shaving functions while being displaceable on the shafts 3 offset from respective axes of symmetry of the additional brushes. Obviously any other suitable connection, as for example, bayonet connection, can be utilized. As is seen in FIG. 6 each shaft 3 is rotatable about a respective axis 3' which is offset relative to an axis of symmetry 41 of the respective member.

Finally, a razor blade 18, 20 is pivotally mounted (FIGS. 1 and 4) on the top of the device for adapting a convenient position chosen by the user. Facilitating the displacement of the razor blade is a lever 20 mounted on the holder 18 and pivotal between working and resting positions in a plane extending transversely to a plane in which the razor blade is movable.

I claim:

1. A massaging device, comprising:

a housing formed with a hollow interior;

means forming a reservoir of a flowable substance in said housing;

pump means in said housing for pumping the substance along a path thereof;

a universal head on said housing and having a center axis;

a plurality of massaging elements formed with respective axes of symmetry extending parallel to the center axis;

actuating means in said housing for actuating said massaging elements and including a plurality of driven shafts rotatable about respective rotation axes extending parallel to said central head axis, each of said massaging elements being mounted rotatably fixedly on a respective driven shaft and having the respective axis of symmetry offset from a respective one of said axes of rotation, said massaging elements being displaceable along respective paths toward and away from said central axis between inner and outer positions and being adjacent one another in said inner position, and magnetic means for generating magnetic vortexes upon displacement of said massaging members between said inner and outer positions.

2. The device defined in claim 1 wherein each of said massaging elements is a removable semi-sphere ball formed with a respective connecting means for connecting said balls with the respective shaft.

3. The device defined in claim 1 wherein said massaging elements are removable brushes formed with connecting means for removably connecting said brushes with said actuating means.

4. The device defined in claim 1 wherein said actuating means includes:

an electric source, a motor connected with said source and formed with a driving shaft extending parallel to said axes of rotation, a first pinion keyed to said driving shaft and having a first diameter, a second pinion having a diameter larger than said first one and meshing with said first pinion, said second pinion being provided with an output shaft, a third pinion mounted rotatably fixedly on said output shaft and having a diameter lesser than said first diameter, and a plurality of fourth pinions mounted on the respective driven shafts and rotatable about said axes of rotation upon meshing said third pinion with said fourth pinions, so that said pinions form a reducer for decreasing a number of revolutions of said motor.

5. The device defined in claim 4 wherein said source is a battery or a rechargeable accumulator.

6. The device defined in claim 4 wherein said actuating means further comprising a double throw switch connected with said source and said motor and mounted on said housing.

7. The device defined in claim 1 wherein said pump means includes a pump provided with a downstream channel immersed in said reservoir and an upstream channel opening into a distributing channel extending transversely to said upstream channel, said distributing channel being provided with a plurality of branches opening outwardly.

8. The device defined in claim 7, further comprising a plurality of brushes formed with respective central openings, each of said openings being in a flow communication with a respective one of said branches.

9. The device defined in claim 1, further comprising a razor blade mounted pivotally on said housing about a pivot axis, said razor blade being provided with a lever mounted pivotally thereon between a working position and a rest position about a lever axis extending generally perpendicular to said pivot axis.

10. The device defined in claim 1 wherein said magnetic means includes said massaging members made of a magnetized material.

11. The device defined in claim 1, wherein said magnetic means includes a plurality of magnetic inserts mounted on said head and juxtaposed with respective massaging members to create said vortexes forming an overlapping magnetic zone in said inner position of the massaging elements.

12. The device defined in claim 1, wherein said massaging elements are formed with means for receiving said magnetic means which includes inserts made of a magnetizable material.

* * * * *